US008840546B2

(12) United States Patent
Truong et al.

(10) Patent No.: US 8,840,546 B2
(45) Date of Patent: Sep. 23, 2014

(54) SYSTEM FOR ACCESSING A BODY ORIFICE

(75) Inventors: Stephanie L. Truong, San Francisco, CA (US); Vandana Jain, Navi Mumbai (IN); Michael Yung Peng, Laguna Niguel, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 379 days.

(21) Appl. No.: 13/150,915

(22) Filed: Jun. 1, 2011

(65) Prior Publication Data
US 2011/0295073 A1    Dec. 1, 2011

Related U.S. Application Data

(60) Provisional application No. 61/396,679, filed on Jun. 1, 2010.

(51) Int. Cl.
*A61B 1/227* (2006.01)

(52) U.S. Cl.
CPC ..................... *A61B 1/227* (2013.01)
USPC ........................................................ 600/187

(58) Field of Classification Search
CPC ............ A61B 1/015; A61B 1/06; A61B 1/07; A61B 1/227
USPC ......... 600/187, 188, 190, 191, 193, 199, 200, 600/245, 246
See application file for complete search history.

(56) References Cited

U.S. PATENT DOCUMENTS

| 3,848,587 | A | 11/1974 | McDonald |
| 5,465,709 | A | 11/1995 | Dickie |
| 5,745,632 | A | 4/1998 | Dreyer |
| 5,916,150 | A | 6/1999 | Sillman |
| 6,190,310 | B1 | 2/2001 | Cook |
| 6,390,975 | B1 | 5/2002 | Walls et al. |
| 6,551,346 | B2 | 4/2003 | Crossley |
| 7,510,524 | B2 | 3/2009 | Vayser |

(Continued)

FOREIGN PATENT DOCUMENTS

| FR | 2 458 266 A1 | 1/1981 |
| GB | 1300055 | 12/1972 |

(Continued)

OTHER PUBLICATIONS

Extended European Search Report dated May 5, 2014 in International Application No. PCT/US2011038790, Applicant: The Board of Trustees of the Leland Stanford Junior University (6 pages).

*Primary Examiner* — Pedro Philogene
*Assistant Examiner* — David Comstock
(74) *Attorney, Agent, or Firm* — Vista IP Law Group, LLP

(57) ABSTRACT

A system for illuminating a body orifice includes: a frusto-conical optical waveguide speculum includes a distal end, a proximal end wider than the distal end, an at least partially circumferential body wall having a bore passing between the proximal and distal ends of the speculum; and a base that couples to the speculum and receives a light source such that the speculum is configured to propagate light from the light source along the body wall. In a preferred embodiment, the body wall defines between an inner and outer surface of the body wall a fluidic channel configured to delivery fluid to the distal end of the speculum and a suction channel configured to drain fluid from distal end of the speculum.

45 Claims, 8 Drawing Sheets

(56) References Cited

U.S. PATENT DOCUMENTS

| | | |
|---|---|---|
| 7,901,353 B2 | 3/2011 | Vayser |
| 2002/0193664 A1 | 12/2002 | Ross |
| 2004/0143167 A1 | 7/2004 | Branch |
| 2007/0276191 A1 | 11/2007 | Selover |
| 2008/0208006 A1 | 8/2008 | Farr |
| 2010/0016787 A1 | 1/2010 | Shapiro |

FOREIGN PATENT DOCUMENTS

| | | |
|---|---|---|
| WO | WO 97/42921 A1 | 11/1997 |
| WO | 2004/019770 | 3/2004 |
| WO | 2009/116969 | 9/2009 |
| WO | 2009116969 A | 9/2009 |

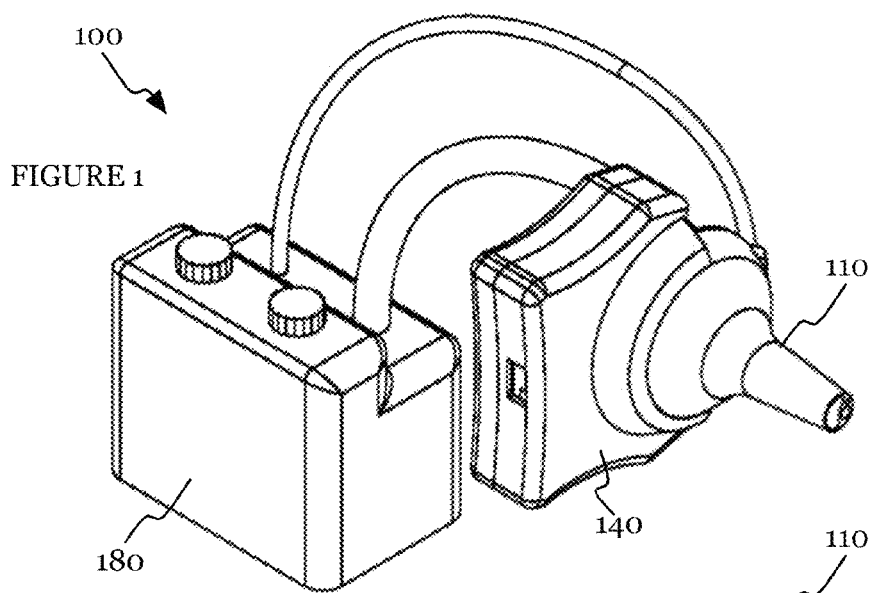
FIGURE 1
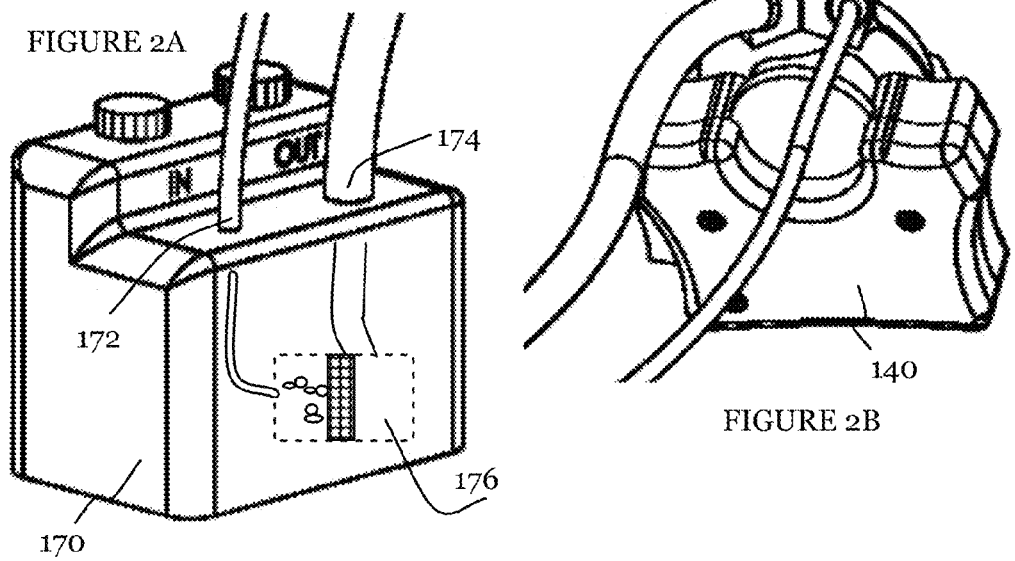
FIGURE 2A
FIGURE 2B

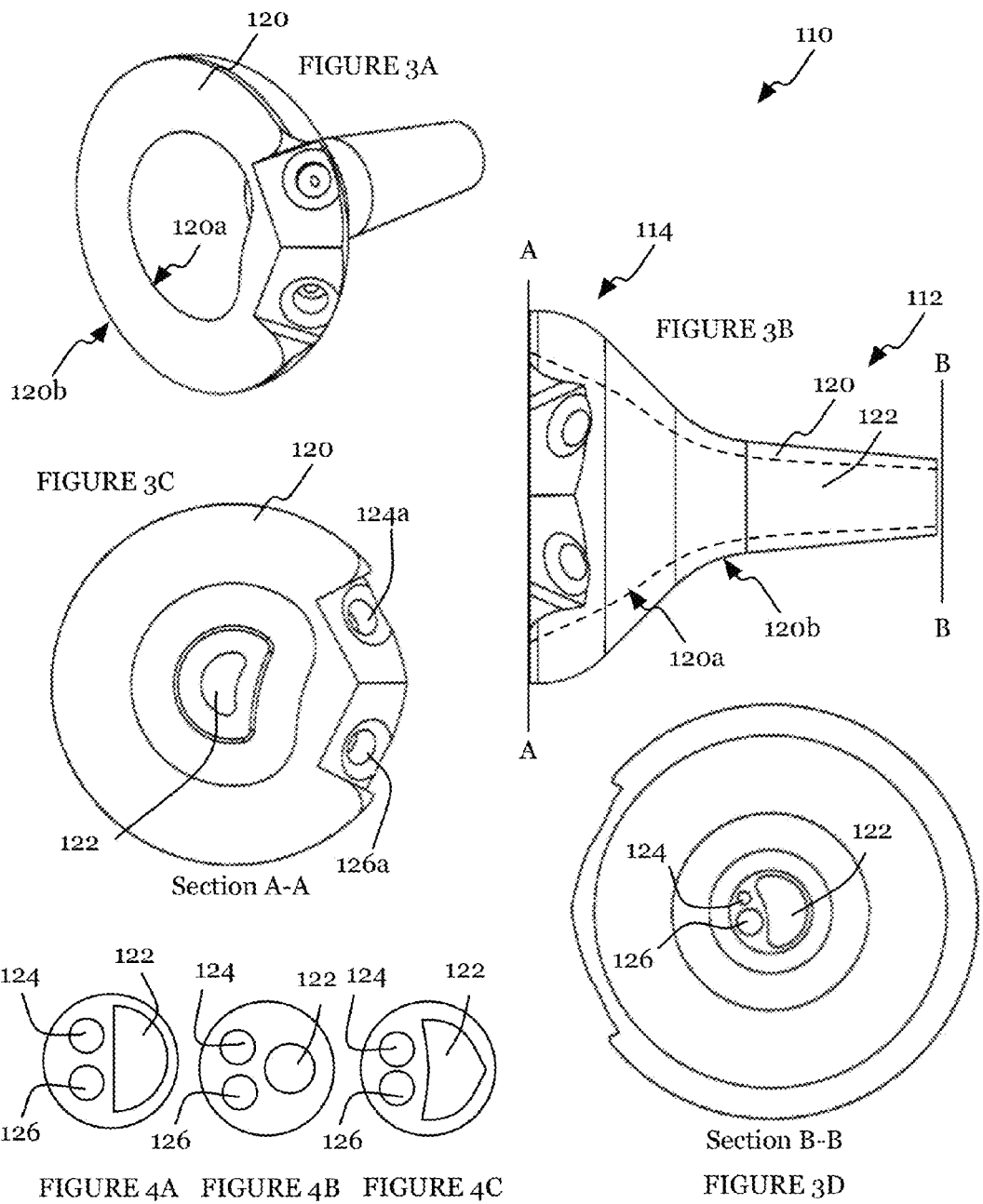

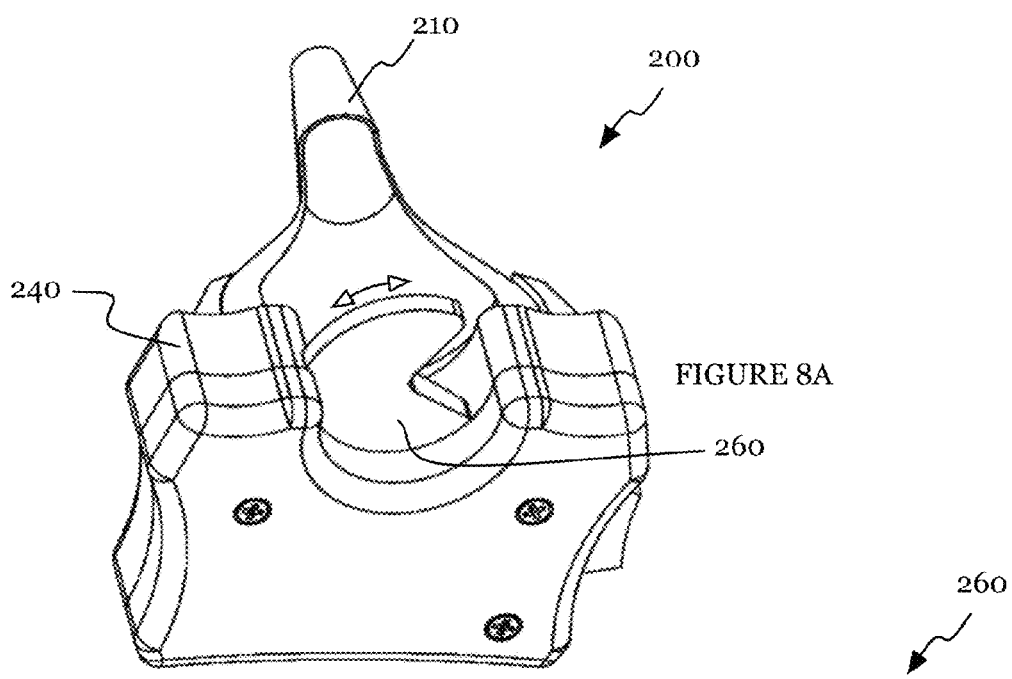
FIGURE 8A
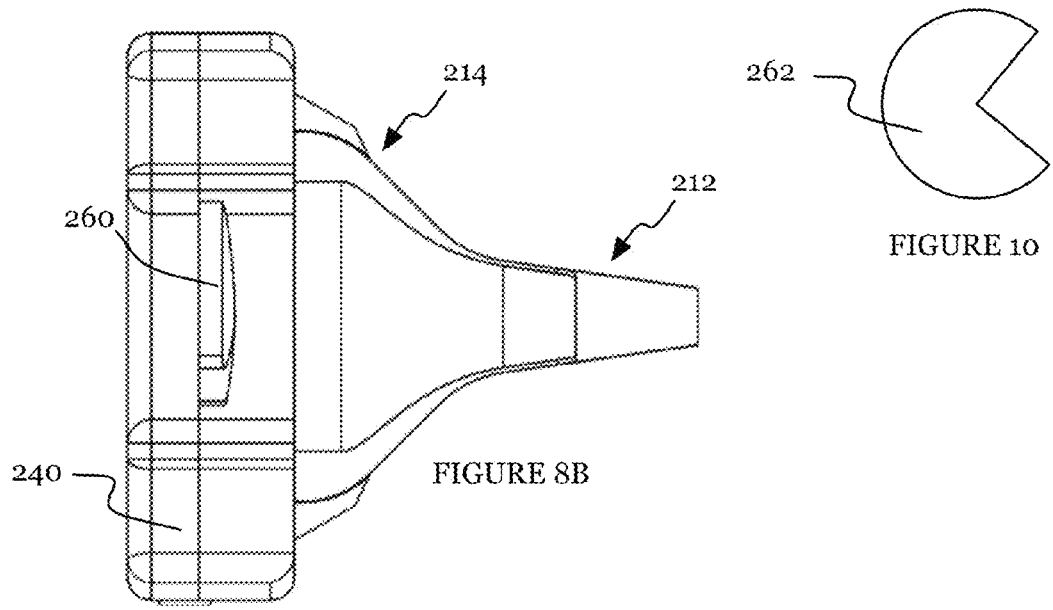
FIGURE 8B
FIGURE 10

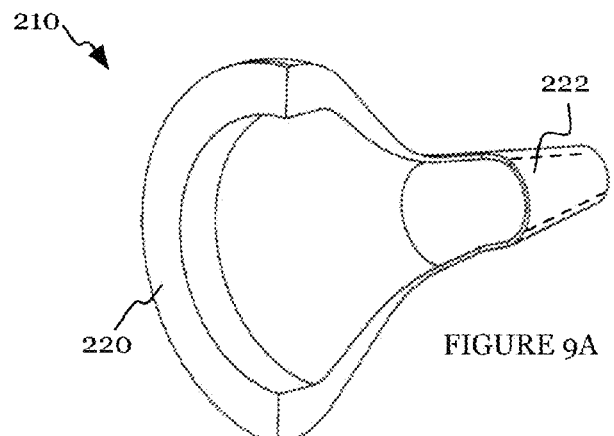
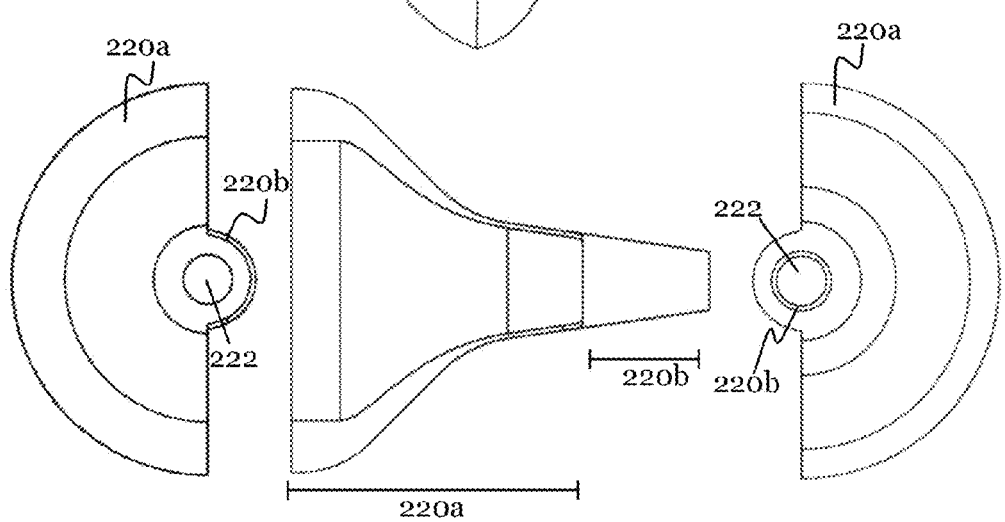
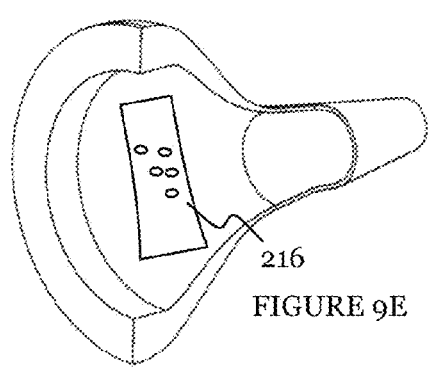

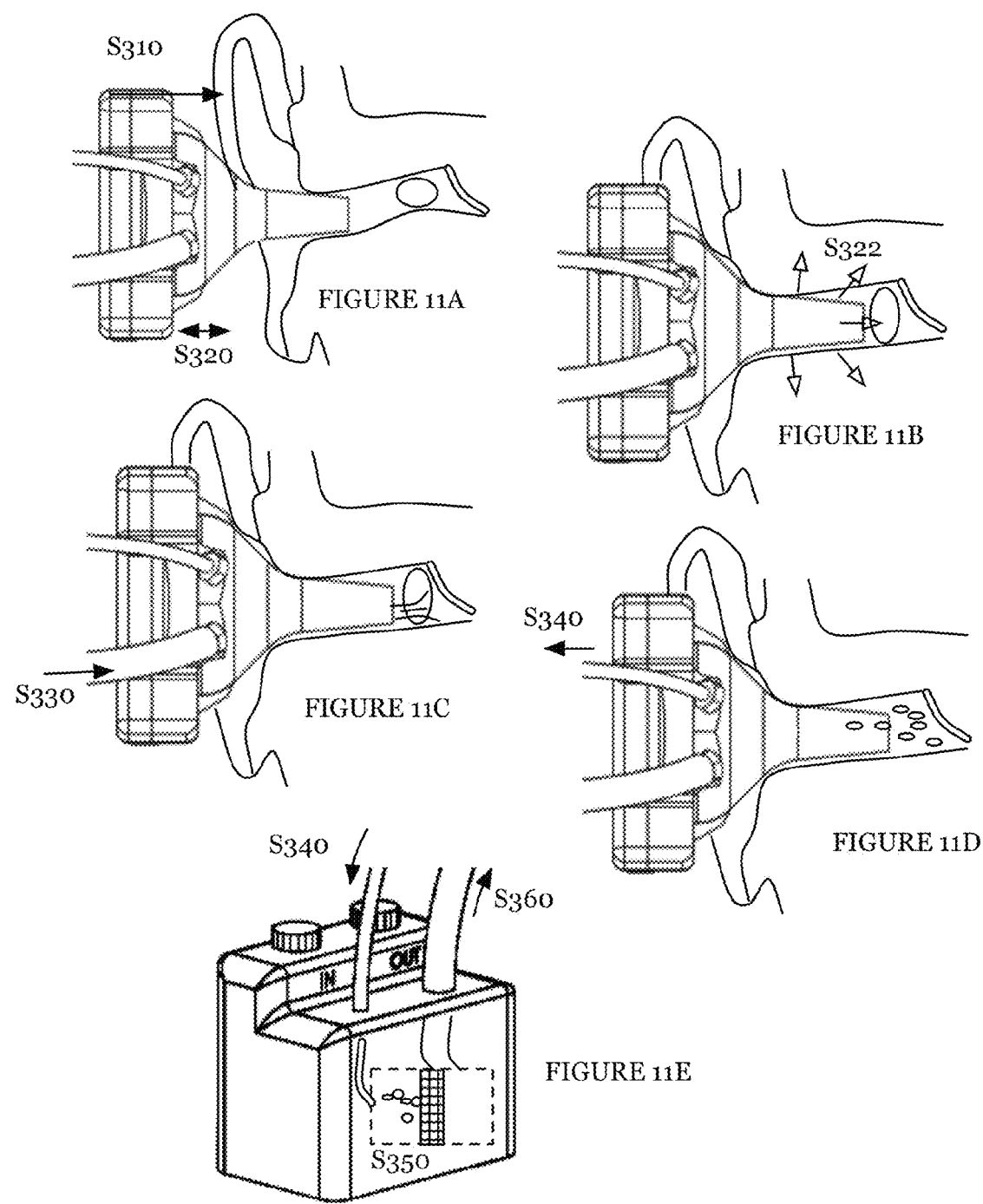

SYSTEM FOR ACCESSING A BODY ORIFICE

CROSS-REFERENCE TO RELATED APPLICATIONS

This application claims the benefit of U.S. Provisional Application No. 61/396,679 filed 1 Jun. 2010, which is incorporated in its entirety by this reference.

GOVERNMENT LICENSE RIGHTS

This invention was made with Government support under contract TW008781 awarded by the National Institutes of Health. The Government has certain rights in this invention.

TECHNICAL FIELD

This invention relates generally to the medical field, and more specifically to an improved system for illuminating a body orifice in the medical field.

BACKGROUND

Ear wax, or cerumen, is a normal secretion that becomes a problem in certain circumstances. For instance, excessive and impacted ear wax is a clinical concern because it can obstruct visualization of the tympanic membrane for health assessments. Furthermore, if ear wax is in contact with the tympanic membrane, it can cause discomfort and occasionally vertigo, tinnitus, or chronic cough. As another example, impacted cerumen may cause a conductive hearing loss, resulting in reduced hearing ability and interfering with formal hearing assessments.

Conventional treatment options for ear wax removal vary in their efficacy, time and safety. One common procedure is use of cotton-tipped swabs to clean the ear, but this is potentially dangerous in that the swab can push ear wax further into the ear, perforate the ear drum, and/or abrade the ear canal. Use of cerumenolytic agents dissolve or soften ear wax and are often used in combination with other ear wax removal treatments, but these agents can only break down the outermost surface of impacted ear wax and are ineffective on deeper portions of ear wax. Another treatment is "ear candling", a process involving placing a hollow candle in the ear canal and lighting one end of the candle, with the intent of allowing heat to create a pressure differential that draws cerumen out of the ear. However, studies have shown that ear candling is ineffective, and is even potentially dangerous. Typically performed by medical practitioners, irrigation is a common procedure that involves expelling fluid from a syringe directly into the ear canal to dislodge and wash out ear wax. However, in its current form, this messy and time-consuming procedure is performed without the ability to visualize or easily control the direction of the fluid, and risks complications such as a perforated ear drum.

Thus, there is a need in the medical field to create an improved system for illuminating a body orifice, especially for removal of an obstruction in the body orifice. This invention provides such improved system for illuminating a body orifice.

BRIEF DESCRIPTION OF THE FIGURES

FIG. 1 is a perspective view of the system of a first preferred embodiment;

FIGS. 2A and 2B are perspective views of the fluidic pump system and the base with speculum, respectively, of the system of a first preferred embodiment;

FIGS. 3A-3D are various views of the speculum of the system of a first preferred embodiment;

FIGS. 4A-4C are schematics of variations of bore cross-sections in the speculum of the system of a first preferred embodiment;

FIGS. 8A-8B are perspective and top views, respectively, of the system of a second preferred embodiment;

FIGS. 9A-9E are various views of the speculum of the system of a second preferred embodiment;

FIG. 10 is a schematic of the magnifier of the base in the system of a second preferred embodiment;

FIGS. 11A-11E are schematics of the method of using the system of a preferred embodiment.

DESCRIPTION OF THE PREFERRED EMBODIMENTS

Figure 5A:
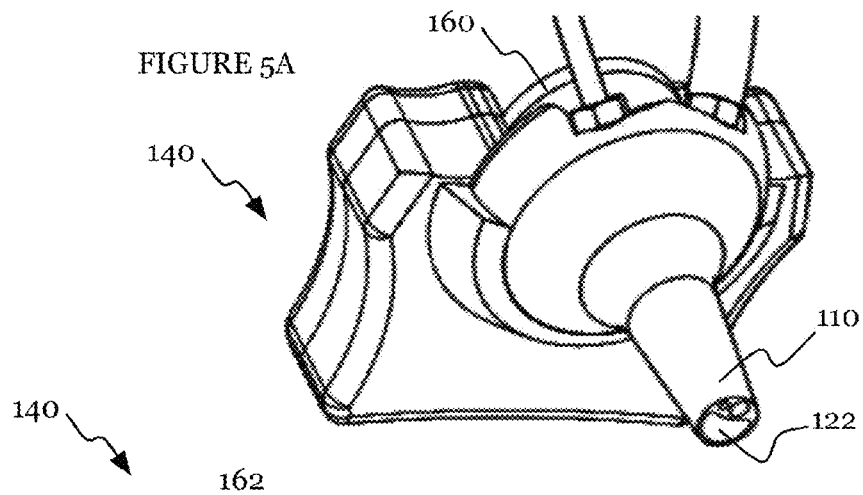
FIGS. 5A-5C are schematics of the base in the system of a preferred embodiment.

The following description of preferred embodiments of the invention is not intended to limit the invention to these preferred embodiments, but rather to enable any person skilled in the art to make and use this invention.

The system for illuminating a body orifice is used to increase visualization of the body orifice, preferably to aid removal of an obstruction in the body orifice. In a preferred embodiment, the system is used to aid removal of ear wax, or cerumen, from an ear canal of a patient. For instance, the system may be used to aid removal of excessive, impacted ear wax, and/or to aid removal of ear wax prior to an audiology exam to increased specificity of the audiology exam. The system is safer, less time-consuming, more comfortable for the patient, and more affordable than conventional ear wax removal treatments. However, although the system is primarily described in the context of ear wax removal from the ear canal, the system may alternatively be used to aid removal of obstructions from any suitable body orifice or passageway, such as the nose or throat. Furthermore, the system may be used to increase visualization of the body orifice for health assessment, or any suitable purpose.

In a first preferred embodiment, as shown in FIGS. 1-5, the system for illuminating a body orifice includes: an optical waveguide speculum 110 including a distal end 112 insertable into the body orifice, a proximal end 114 wider than the distal end 112, and an at least partially circumferential body wall 120 defining a bore 122 passing from the proximal end 114 of the speculum to the distal end 112 of the speculum; and a base 140 that couples to the proximal end 114 of the speculum and receives a light source 150 adjacent to the speculum, such that the speculum no is configured to propagate light from the light source along the body wall 120, thereby illuminating the body orifice. The body wall 120 of the speculum includes an inner surface and an outer surface, and defines at least partially between the inner and outer surfaces a fluidic channel 124 configured to deliver fluid from the proximal end 114 of the speculum to the distal face of the speculum, and a suction channel 126 configured to drain fluid from the distal face of the speculum to the proximal end 114 of the speculum.

In a preferred embodiment, the speculum no is designed to be disposable or used a limited number of times (e.g. disposed after use with one patient) and the base 140 is designed to be reusable (e.g. for use with multiple patients). In other embodiments, the speculum and the base are both designed to be reusable (e.g. sterilized between multiple patients) or the speculum and base are both designed to be disposable or used a limited number of times.

The speculum no functions to propagate or carry light throughout its body, thereby illuminating the body orifice when the speculum no is inserted in the body orifice. The speculum 110 may further function to manipulate the structure of the body orifice. For example, in a preferred embodiment the speculum no may straighten the ear canal when inserted into the ear canal. As shown in FIGS. 3A-3D, the speculum preferably has an approximately frustoconical body shape, with a distal end 112 insertable into the body orifice, a proximal end 114 wider than the distal end 112, and at least a partial circumferential body wall 120 having an inner surface 120a and an outer surface 120b. The body wall 120 may be thicker at the proximal end 114 of the speculum than at the distal end 112 of the speculum. As best shown in FIG. 3B, the speculum body may include an elongated neck portion between the proximal and distal ends, such that the body wall 120 has approximately the same diameter or width along the neck portion. The diameter of the neck portion may be approximately equal to, or slight larger than, the diameter of the distal end of the body, and substantially narrower than the proximal end 114 of the body. However, the neck portion of the speculum body may have any suitable diameter, and the speculum may be any suitable general shape.

The speculum body is preferably an optical waveguide such that it propagates light throughout its body due to total internal reflection and/or other 134 material properties. The speculum body may be made of a transparent polymeric material such as acrylic or polycarbonate, or of another suitable light-propagating material such as glass. The speculum body may be manufactured in an injection molding process, machining process, or any suitable process.

The speculum body, in particular the inner surface 120a of the body wall 120, defines a bore 122 passing from the proximal end 114 of the body to the distal end of the body. The bore 122 provides a passageway through which the body orifice may be more easily visualized, through the sides of the body wall 120 and/or through the distal end 112 of the speculum body. For example, the user may view the body orifice from the proximal end of the speculum (FIG. 3C). The proximal end and distal end of the body are preferably open such that the bore 122 is a through hole on both ends, but alternatively the proximal and/or distal end of the body may be closed such that the bore is a blind hole or a hollow cavity closed on both ends. As shown in FIG. 3B, similar to the overall shape of the speculum body, the bore 122 is preferably wider at a proximal end 114 than at the distal end 112.

As shown in FIG. 3A, the body wall 120 preferably defines at least partially between the inner and outer surfaces of the body wall a plurality of channels. Some or all of the channels may be contoured to follow the curvature of the frustoconical body. The plurality of channels includes a fluidic channel 124 configured to delivery fluid from the proximal end of the body to the distal face, and a suction channel 126 configured to drain fluid from the distal face to the proximal end of the body. The plurality of channels may further include any suitable kind of channel such as for guiding an extraction tool used for manually removing or dislodging an obstruction in the orifice. The fluidic channel 124 enables a medical practitioner or other user to irrigate or introduce fluid into the body canal, such as for dislodging at least a portion of an obstruction (e.g., some or all of impacted ear wax in the ear canal) or cleaning the body orifice. The suction channel 126 enables the user to drain or remove the fluid from the introduced fluid from the body canal, any dislodged portions of the obstruction, and/or other particles, preferably through suction or other pressure differential. The fluid and particles may additionally and/or alternatively be removed through continued flushing of fluid into the body orifice, gravity, or any suitable manner.

Figure 7:
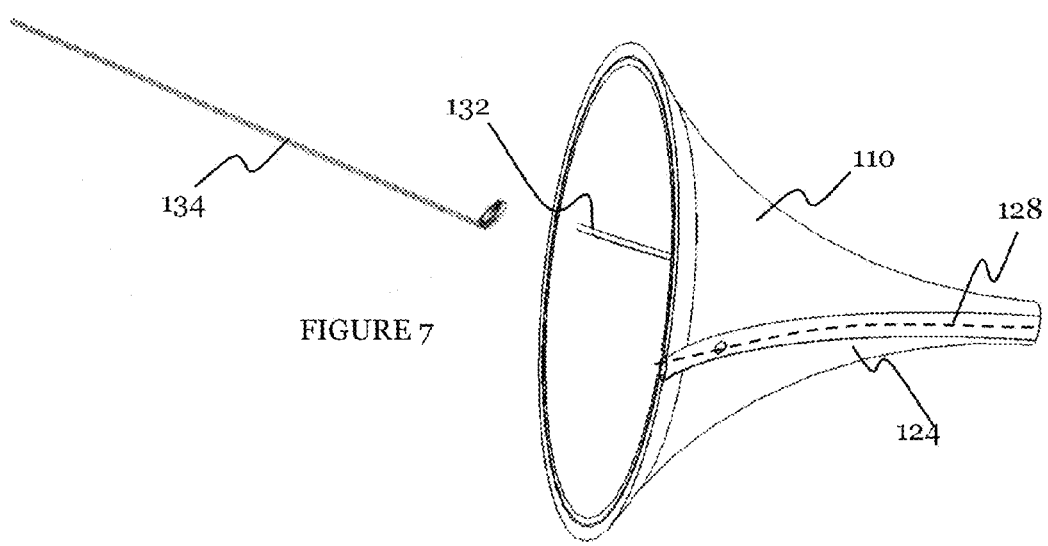
FIG. 7 is a variation of the speculum in the system of a first preferred embodiment.

The fluidic channel 124 and suction channel 126 preferably extend fully from a proximal face on the proximal end 114 of the speculum 110 to a distal face on the distal end 112 of the speculum 110. The fluidic channel 124 preferably has an inlet 124a on the proximal end of the speculum that couples to a fluid supply, and the suction channel 126 preferably has an inlet 126a on the proximal end of the speculum that couples to a fluid receptacle. However, one or more of the plurality of channels may depart from the body wall 120 at some location along the channel length. For instance, as shown in FIG. 7, rather than terminating at a proximal face at the proximal end 114 of the body wall 120, the fluidic channel 124 or suction channel 126 may terminate on the side of the body wall. In an alternative variation, the fluidic channel 124 and suction channel 126 may be at least partially external or separate from the speculum. For instance, the fluidic channel and/or suction channel may include separate tubing that are coupled to the inner surface, outer surface, or within the body wall of the speculum, to carry fluid to and from the body orifice.

The fluidic channel 124 and suction channel 126 may be similar in diameter, but one of the channels may be slightly larger than the other. Furthermore, each channel may be of uniform diameter or varying diameter along its length. For example, the distal end 112 of the fluidic channel 124 may be narrowed, similar to a nozzle to influence flow rate and/or force of the fluid exiting the fluidic channel 124. The channels may further include fluid control elements such as valves to modulate fluid flow rate.

The fluidic and suction channels are preferably generally smaller in diameter than the bore 122. At the distal end 112 of the speculum body (such as on the most distal planar face), the bore 122 has a larger cross-sectional area than the cross-sectional area of the fluidic channel 124 and the suction channel 126, which may help increase visualization of the body orifice. In a preferred variation, as shown in FIG. 3D, at the distal end 112 of the speculum body the bore 122 preferably has an approximate lune shape that is more than half the cross-sectional area of the speculum 110. However, as shown in FIGS. 4A-4C, the bore 122 may have a circular, semi-circular, or other suitable cross-sectional shape. The fluidic channel 124 and suction channel 126 may be located such that on the distal end 112 of the speculum body, the cross-sections of the fluidic and suction channels are located in the concavity of the lune cross-section of the bore 122. However, the bore, fluidic channel 124, and suction channel 126 may alternatively have any suitable shape and relative size.

Figure 5B:
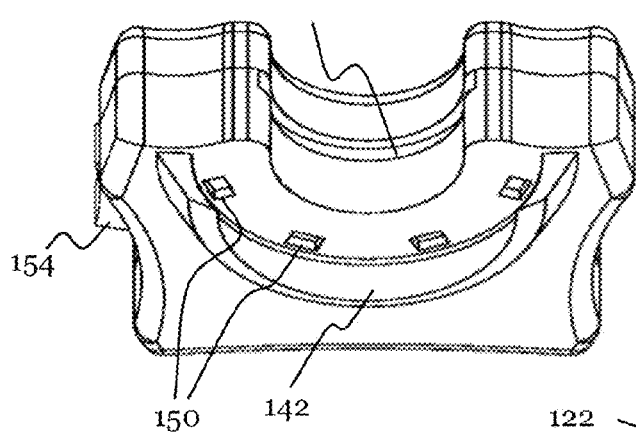

The base 140 of the system functions to illuminate the speculum 110, and may further function to provide a handhold for the user of the system. As shown in FIGS. 5A and 5B, the base 140 couples to the speculum 110 and receives (e.g., include or be coupled to) a light source such that the speculum 110 propagates light from the light source through the speculum body, thereby illuminating the body orifice when inserted in the orifice. The base 140 may further receive a magnifier aligned with the bore 122 that magnifies the view of the ear canal or other body orifice.

Figure 5C:
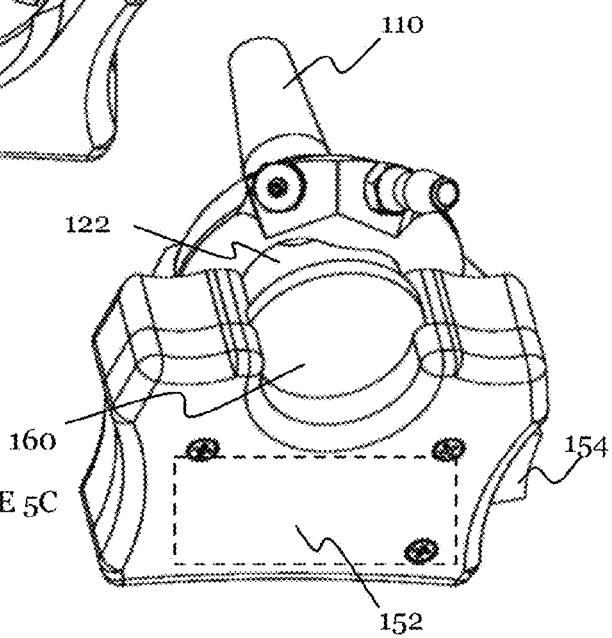

In one preferred embodiment, as shown in FIGS. 5A-5C, the base 140 is a handheld enclosure. The base 140 may include hand contours, such as side contours, to better accommodate a handheld grasp of the base by the user. The base 140 preferably includes a cradle 142, slot, or other receptacle to which the speculum 110 couples. For example, the cradle 142 may be arcuate to receive the circular proximal portion of the speculum 110. The base 140 and speculum 110 may removably couple to one another based on interference from relative dimensions such as with a snap fit, and/or may removably couple to one another with a fastener such as threads, pins, clips, latches, straps, tabs and slots, adhesive, or any suitable means for coupling. In another variation, the base 140 and speculum no may be more permanently coupled to one another (e.g. press fit or permanent adhesive).

In one preferred variation, the base 140 preferably receives a plurality of light sources 150 integrated in the base 140 and arranged such that the lights are adjacent to the proximal end 114 of the speculum no, such as within the cradle or other part of the base 140 that couples to the speculum no. The light sources may include light-emitting diodes (LEDs), optical fibers, fluorescent materials, or any suitable light source. As shown in FIG. 5B, in a preferred embodiment, the plurality of light sources are coupled to or embedded behind the cradle 142 of the base, such that a proximal face of the speculum no receives light from the light sources. In this embodiment, the light sources are in an arcuate arrangement adjacent to at least a portion of the circumferential body wall 120, and may be spaced circumferentially equally apart such that the speculum 110 propagates light in a more uniform matter. However, the light sources may be in any suitable arrangement along the base.

The base 140 preferably includes electronics 152 that power and control the light sources. For example, the electronics may include user controls that power the light sources on and off, such as a switch 154 on a side contour for easy user accessibility. Other user controls may include switches, sliders, or other interactive elements that adjust light intensity, light color, and/or any suitable characteristic of the light sources. Furthermore, the electronics 152 may include controls for selectively powering only a particular portion of the light sources, to increase positional control of the light that is passed to the speculum 110. The electronics may also include a power source such as a battery, circuitry for recharging the battery (e.g. a mini-USB port or other suitable powering interface), and/or lights or other signals to indicate the amount of charge left for powering the light sources. As shown in FIG. 5C, circuit boards and/or another portion of the electronics 152 may be enclosed within two coupleable portions of the base, but may alternatively be in any suitable location.

In an alternative variation, the base 140 may receive or couple to one or more external light sources. For instance, the base may include a slot or other light receptacle that receives an external ring of lights, handheld flashlight, or any suitable external light sources to be placed adjacent to the speculum 110. Furthermore, the base may include optical fibers, mirrors, or any other suitable light-directing elements that direct light to the speculum 110.

The magnifier 160 of the base 140 functions to magnify the view of the body orifice and/or obstructions in the body orifice. The magnifier 160 is coupled to base 140 proximate to the speculum 110, and preferably aligned with the bore 122 of the speculum. In a preferred variation, as shown in FIG. 5C, the magnifier 160 is an optical lens system. For example, the optical lens system may include a single convex lens (e.g. providing 10× or any suitable level of magnification) or a dual lens system with lenses placed in series. In another example, the optical lens system includes multiple lenses placed in a binocular setup for viewing with two eyes. The magnifier 160 is preferably inserted in a slot 162 in the base. The magnifier may be rotatable in the base, such as to allow the user to adjust the position and/or orientation of the magnifier.

Figure 6:
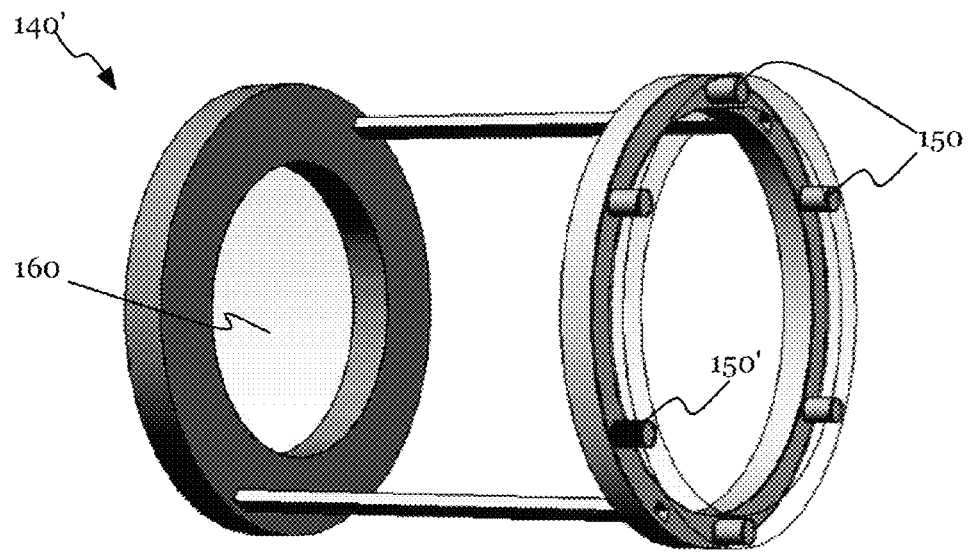
FIG. 6 is a variation of the base in the system of a preferred embodiment.

In an alternative embodiment of the base, the base 140' is a frame or any suitable structure that couples to the speculum 110, receives or includes a plurality of light sources, and/or includes a magnifier 160 aligned with the speculum 110, similar to the handheld enclosure embodiment of the base. For example, as shown in FIG. 6, the base is a frame having a first end that includes a magnifier and a second end that includes a ring of light sources. The light sources may be a ring of LEDs encased in a plastic ring or other protective cover. The second end couples directly to the speculum 110, such that the speculum 110 receives and propagates light from the light sources on the second end of the frame. The frame may be approximately cylindrical, a rectangular prism, or any suitable shape.

The system of the first preferred embodiment may further include a fluid pump system 170 that functions to control flow of fluid through the fluidic channel 124 and/or suction channel 126. The fluid pump system 170 is preferably coupled to at least the fluidic channel 124 and a fluid supply (e.g. container of water, saline, or other suitable fluid for irrigation or other purposes) and controls fluid flow from the fluid supply through the fluidic channel. The fluid pump system is preferably further coupled to the suction channel. In other words, as shown in FIGS. 2A and 2B, the fluid pump system is preferably a closed fluidic system with an outlet 174 that introduces fluid into the body orifice through the fluidic channel 124 of the speculum and an inlet 172 that receives fluid from the body orifice through the suction channel 126 of the speculum. Such a closed fluidic system may be advantageous to reduce mess and hassle of an irrigation procedure. The fluidic pump system may include a positive displacement pump such as a peristaltic pump, or any suitable kind of fluid pump or flow actuator. In alternative variations, the fluidic pump system may include manually-powered flow actuators such as a syringe or hand pump.

In some variations, the closed fluidic system may further include a filter 176 that removes particles from the drained fluid and recirculate the filtered fluid to the body orifice through the fluidic channel 124. For example, the filter may include a mesh screen, valves, a centrifuge, or any suitable filtering means to remove particles (e.g. dislodged ear wax, dirt, or skin particles) from the drained fluid. The filter may be coupled directly to the flow actuator, tubing, or any suitable portion of the fluidic pump system.

In one variation of this embodiment, as shown in FIG. 7, the speculum 110 or other portion of the system further includes a tool guide 132, passing along the speculum towards the distal end 112 of the speculum, that helps guide and provide controlled movement of an extraction tool 134 used for removing obstructions in the body orifice. The extraction tool 134 is preferably a thin-handled, elongated tool with a tip adapted to capture or dislodge the obstruction, such as an angled curette tip, a hook tip, or forceps. The tool guide may be one or more of several variations. In a first variation, the tool guide is a groove, such as a linear slot, having a width approximately the width of (preferably slightly wider than) the extraction tool. In a second variation, the tool guide is an enclosed channel within the body of the wall, similar to the fluidic and suction channels. In a third variation, the tool guide is an external channel coupled to the inner surface or outer surface of the body wall 120 of the speculum. In any of these variations, the tool guide and/or extraction tool may include a stopper or other mechanisms that limit the extent to which the extraction tool may enter the stopper, thereby limiting the extent to which the extraction tool may enter the body orifice. For example, when the system is used to remove impacted ear wax or other obstructions in the ear canal, a portion of the extraction tool may abut a portion of the tool guide to help prevent the extraction tool from extending too far into the ear canal and causing damage to the ear drum. Furthermore, in any of these variations, the tool guide and/or extraction tool may include ruled, measured tick marks or indications that allow the user to monitor the extent to which the extraction tool is inserted.

In another variation of this embodiment, as shown in FIG. 7, the fluidic channel 124 and/or suction channel 126 may include a targeting mechanism 128 that indicates the location that the fluidic channel 124 will introduce or drain fluid, which may be useful to strategically aim the jet of fluid from the fluidic channel at a particular location. In one variation, the fluidic channel and/or suction channel may include an optical fiber, approximately centrally located within the channel, that propagates a light signal to a precise point within the body orifice. The light signal from the targeting mechanism is visible to the user through the bore, such as for targeting a particular portion of impacted ear wax for irrigation and dislodgement. However, the targeting mechanism may be any suitable mechanism. In this variation, as shown in FIG. 6, the light sources coupled to the base may include a targeting light source 150' aligned with the optical fiber or other light-receiving targeting mechanism in the fluidic channel 124 and/or suction channel 126, and the targeting light source may be a different color than the other light sources to clearly distinguish the targeting light from the illuminating light propagated by the speculum body.

In a second preferred embodiment, as shown in FIGS. 8 and 9, the system 200 for illuminating a body orifice includes: an optical waveguide speculum 210 with an approximately frustoconical profile and including a distal end 212 insertable into the body orifice, a proximal end 214 wider than the distal end, a body wall 220 with a fully circumferential portion 220b and a partially circumferential portion 220a; and a base 240 that couples to the proximal end of the speculum 210 and receives a light source adjacent to the speculum 210. Similar to the first embodiment, the speculum 210 is configured to propagate light from the light source along the body wall. The system of the second preferred embodiment is preferably similar to that of the first preferred embodiment, except as described below. In particular, the system of the second preferred embodiment may lack the fluidic channel and/or suction channel of the first embodiment. The speculum 210 of the second preferred embodiment may be used to illuminate and gain access to a body orifice, such as in applications in which irrigation for removing an obstruction is not necessary or in which an external irrigation system (such as a manually-controlled syringe placed within the speculum) may be used.

In the second preferred embodiment, the speculum 210 is preferably similar to that of the first preferred embodiment, except as described below. As shown in FIGS. 9A-9D, the speculum 210 preferably includes a generally frustoconical profile and includes a body wall 220 with a fully circumferential portion 220b proximate to the distal end 212 of the body and a partially circumferential portion 220a proximate to the proximal end 214 of the body. The fully circumferential portion 220a preferably defines a bore 222. The partially circumferential portion 220a preferably is a "cutaway" portion of the frustoconical shape of the speculum 210, that may function to allow for greater an easier access into the bore and inner surface of the speculum. The partially circumferential portion 220a is preferably a longer portion of the speculum than the fully circumferential portion 220b, but the two portions may have any relative lengths. As shown in FIGS. 9B and 9D, the profile of the partially circumferential portion of the body wall is an arc measuring less than 270 degrees, and more preferably of approximately 180 degrees (i.e. the partially circumferential portion extends approximately halfway around the circumference of the frustoconical speculum shape).

In one variation, the speculum 210 may further include a debris collector 216 that collects particles dislodged by irrigation or other processes for removal of obstructions in the body orifice. For example, as shown in FIG. 9E, the debris collector may a lower or circumferential channel on the proximal portion of the speculum that receives gauze, an adhesive gel membrane, cup, or other receptacle. The debris collector preferably captures and contains particles (e.g. ear wax) that falls and/or is washed out of the body canal through the speculum.

The base 240 of the second preferred embodiment is preferably similar to that of the first preferred embodiment, except that the magnifier 260 of the second preferred embodiment may have a cutout, such as for more visibility into the bore of the speculum 210 and/or greater physical access into the speculum. In a preferred variation, the magnifier 260 includes a circular segment 262 of an optical lens. For example, as shown in FIG. 10, the magnifier 260 is a circular lens with approximately one quarter removed. The magnifier is preferably rotatable within the base, which may allow the user to adjust the orientation of the cutout in the magnifier.

Additional embodiments of the system include any combination of aspects of the first and second preferred embodiments, including any combination of the variations of the speculum, base, fluidic channel, suction channel, light sources, magnifier, and fluidic pump systems. For example, the speculum of the first preferred embodiment may include a debris collector similar to the speculum of the second preferred embodiment. As another example, the speculum of the second preferred embodiment may include a fluidic channel and/or suction channel similar to the speculum of the first preferred embodiment.

Figure 12:
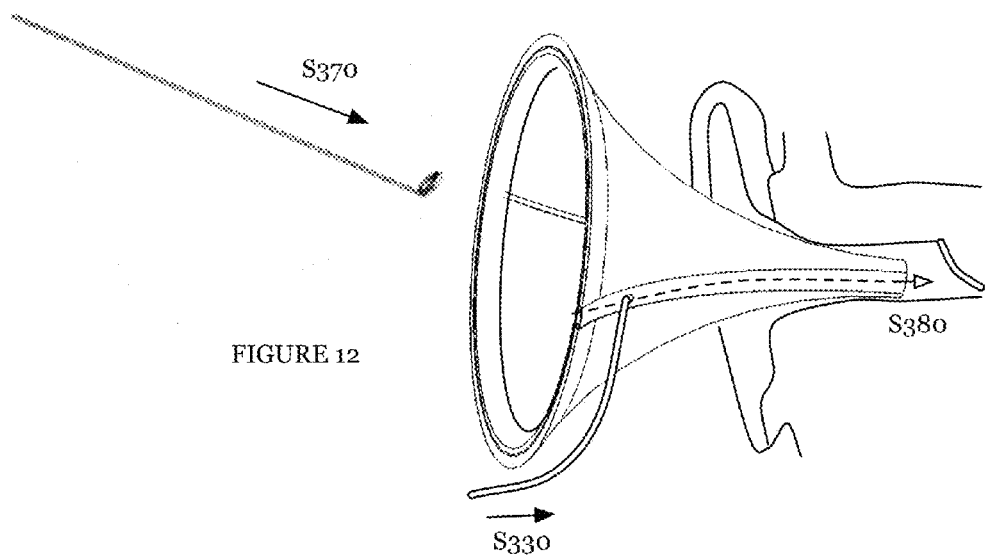
FIG. 12 is a schematic of the steps of an optional step in the method of using the system of a preferred embodiment.

As shown in FIGS. 11A-11E, a method 300 of using the system of the first preferred embodiment to remove an obstruction in a body orifice includes the steps of: inserting a distal end of an approximately frustoconical optical waveguide speculum into the body orifice S310; coupling a proximal end of the speculum to a light source S320; allowing the inserted speculum to propagate light from the light source S322, thereby illuminating at least a portion of the body orifice; directing fluid through a fluidic channel S330 coupled to the speculum into the body orifice, thereby dislodging at least a portion of the obstruction from the body orifice; draining pumped fluid and the dislodged obstruction from the body orifice S340 through a suction channel coupled to the speculum; filtering the drained fluid S350; and redirecting the filtered fluid through the fluidic channel S260 into the body orifice. In some embodiments, as shown in FIG. 12, the method may further include guiding an extraction tool towards the obstruction S370 and/or indicating a targeted location of directed fluid S380. For example, indicating a targeted location of directed fluid may include coupling a second light source to a second waveguide and allowing the waveguide to propagate light from the second light source towards the targeted location of directed fluid. A method of using the system of the second preferred embodiment may be similar to method 300, except the method of using the system of the second preferred embodiment may omit the steps of directing fluid through a fluid channel, draining the pumped fluid, filtering the drained fluid, and redirecting the filtered fluid. However, the method of using the second preferred embodiment may additionally and/or alternatively include manually providing fluid into the speculum such as with a syringe.

As a person skilled in the art will recognize from the previous detailed description and from the figures and claims, modifications and changes can be made to the preferred embodiments of the invention without departing from the scope of this invention defined in the following claims.

We claim:

1. A system for accessing a body orifice, comprising:
    a speculum including:
        a distal end insertable into the body orifice, the distal end having a port;
        a proximal end wider than the distal end;
        an at least partially circumferential body wall defining a bore passing from the proximal end of the speculum to the distal end of the speculum, wherein the body wall includes an inner surface that defines the bore and an outer surface;
        an opening at the body wall, wherein the opening is in fluid communication with the bore defined by the inner surface of the body wall; and
        a fluidic channel located in the body wall, the fluidic channel configured to deliver fluid from the proximal end of the speculum to the distal end of the speculum for dislodging debris within the body orifice; and
    a base that couples to the proximal end of the speculum and is configured to provide light towards the speculum.

2. The system of claim 1, wherein the body wall further defines between the inner and outer surfaces a tool channel that is configured to receive and guide an extraction tool along the speculum adjacent to the bore.

3. The system of claim 1, wherein the fluidic channel includes a targeting mechanism that indicates a location of fluid delivery by the fluidic channel.

4. The system of claim 3, wherein the targeting mechanism is an optical fiber.

5. The system of claim 1, wherein the base includes an arcuate cradle that receives the proximal end of the speculum.

6. The system of claim 5, wherein the speculum couples to the base with a snap fit.

7. The system of claim 1, further comprising one or more light sources arranged on the base.

8. The system of claim 7, wherein the one or more light sources include a plurality of light sources in an arcuate arrangement adjacent to the proximal end of the speculum.

9. The system of claim 8, wherein the one or more light sources include a light emitting diode (LED).

10. The system of claim 8, wherein the one or more light sources include at least two light sources configured to provide lights of at least two different colors.

11. The system of claim 1, further comprising a magnifier coupled to the base proximate to the speculum.

12. The system of claim 11, wherein the magnifier includes an optical lens substantially axially aligned with the bore of the speculum.

13. The system of claim 12, wherein the magnifier includes at least two optical lenses.

14. The system of claim 1, further comprising a fluid pump system that is coupled to the fluidic channel and a fluid supply, wherein the fluid pump system controls flow of fluid from the fluid supply.

15. The system of claim 14, wherein the fluid pump system is further coupled to a suction channel, the fluid pump system including a filter that filters drained fluid; and wherein the fluid pump system is configured to recirculate the filtered drained fluid to the fluidic channel.

16. The system of claim 1, wherein the body wall itself is an optical waveguide that is configured to propagate the light along the body wall.

17. The system of claim 1, wherein the at least partially circumferential body wall comprises a complete circumferential body wall.

18. The system of claim 1, wherein the proximal end comprises a closed end.

19. The system of claim 1, wherein the opening extends from the inner surface of the body wall in a direction of a thickness of the body wall.

20. A system for accessing a body orifice, comprising:
    a speculum with a tapering profile and including:
        a distal end insertable into the body orifice, the distal end having a port;
        a proximal end wider than the distal end; and
        a wall structure including a fully circumferential wall proximate to the distal end of the body, and a partially circumferential wall proximate to the proximal end, the partially circumferential wall having a cross sectional profile that extends less than a full circumference, wherein each of the fully circumferential wall and the partially circumferential wall comprises a part of an exterior surface of the wall structure;
        wherein the fully circumferential wall defines a bore passing to the distal end of the speculum; and
    a base that couples to the proximal end of the speculum and and is configured to provide light towards the speculum.

21. The system of claim 20, wherein the speculum is made of a polymeric material.

22. The system of claim 20, wherein the base includes an arcuate cradle that receives the proximal end of the speculum.

23. The system of claim 20, wherein the speculum couples to the base with a snap fit.

24. The system of claim 20, further comprising one or more light sources arranged on the base.

25. The system of claim 24, wherein the one or more light sources comprises a plurality of light sources in an arcuate arrangement adjacent to the proximal end of the speculum.

26. The system of claim 24, wherein the one or more light sources include a light emitting diode (LED).

27. The system of claim 20, further comprising a magnifier coupled to the base.

28. The system of claim 27, wherein the magnifier includes an optical lens.

29. The system of claim 28, wherein the optical lens is a circular segment.

30. The system of claim 28, wherein the optical lens is substantially aligned along a longitudinal axis with the bore of the speculum.

31. The system of claim 30, wherein the optical lens is rotatable around the longitudinal axis.

32. The system of claim 30, wherein the optical lens is a circular segment measuring approximately 270 degrees.

33. The system of claim 20, wherein the wall structure itself is an optical waveguide that is configured to propagate the light along the wall structure.

34. The system of claim 20, wherein the partially circumferential wall has a length measured along a longitudinal axis of the speculum that is longer than a length of the fully circumferential wall.

35. A speculum for accessing a body orifice, comprising a body with a tapering profile including:
    a distal end insertable into the body orifice, the distal end having a port;

a proximal end wider than the distal end;
a wall structure including a fully circumferential wall proximate to the distal end of the body; and a partially circumferential wall proximate to the proximal end of the body, the partially circumferential wall having a cross sectional profile that extends less than a full circumference, wherein each of the fully circumferential wall and the partially circumferential walls comprises a part of an exterior surface of the wall structure;
wherein the fully circumferential wall defines a bore passing to the distal end of the speculum.

36. The speculum of claim 35, wherein a cross section of the partially circumferential wall is an arc measuring less than 270 degrees.

37. The speculum of claim 35, wherein the cross section of the partially circumferential wall is an arc of approximately 180 degrees.

38. The speculum of claim 35, wherein the partially circumferential wall is thicker than the fully circumferential wall.

39. The speculum of claim 35, wherein the wall structure itself is an optical waveguide that is configured to propagate light along the wall structure.

40. The speculum of claim 35, wherein the partially circumferential wall has a length measured along a longitudinal axis of the speculum that is longer than a length of the fully circumferential wall.

41. A speculum for accessing a body orifice, comprising:
a body including:
 a distal end insertable into the body orifice, the distal end having a port;
 a proximal end wider than the distal end;
 a circumferential body wall having an inner surface and an outer surface, wherein the inner surface of the body wall defines a bore passing from the proximal end of the body to the distal end of the body;
 an opening at the body wall, wherein the opening is in fluid communication with the bore defined by the inner surface of the body wall; and
a fluidic channel extending from the proximal end of the body to the distal end of the body, the fluidic channel located between the inner surface and the outer surface of the body wall.

42. The speculum of claim 41, wherein the opening extends from the inner surface of the body wall in a direction of a thickness of the body wall.

43. The speculum of claim 41, wherein the circumferential body wall is thicker at the proximal end than at the distal end.

44. The speculum of claim 41, wherein the body wall itself is an optical waveguide that is configured to propagate light along the body wall.

45. The speculum of claim 41, wherein the proximal end comprises a closed end.

* * * * *